United States Patent [19]

Croan et al.

[11] Patent Number: 5,356,624
[45] Date of Patent: Oct. 18, 1994

[54] BIOLOGICAL TREATMENT FOR CONTROLLING WOOD DETERIORATING FUNGI

[75] Inventors: Suki C. Croan; Terry L. Highley, both of Madison, Wis.

[73] Assignee: The United States of America as represented by the Secretary of Agriculture, Washington, D.C.

[21] Appl. No.: 51,716

[22] Filed: Apr. 23, 1993

[51] Int. Cl.$^5$ .............................................. A01N 63/00
[52] U.S. Cl. ............................. 424/93.43; 435/252.1; 435/253.5; 435/904; 424/657
[58] Field of Search ............... 435/252.1, 252.2, 253.5; 424/93 G, 657

[56] References Cited

U.S. PATENT DOCUMENTS

| | | | |
|---|---|---|---|
| 2,516,080 | 7/1950 | Sobin et al. | 167/65 |
| 2,963,401 | 12/1960 | Davisson et al. | 167/65 |
| 3,377,242 | 4/1968 | Lefemine et al. | 167/65 |
| 4,996,149 | 2/1991 | Jarreau et al. | 435/119 |

OTHER PUBLICATIONS

Croan, et al., "Biological Control of Sapwood–Inhabiting Fungi By Living Bacterial Cells of *Streptomyces rimosus* as a Bioprotectant," Abstract, prepared for the May 10–15, 1992 meeting of the International Research Group on Wood Preservation, Harrowgate, U.K., believed to be distributed in Feb. or Mar. of 1992.

Croan, et al., "Synergistic Effect of Boron on *Streptomyces rimosus* Metabolites in Preventing Conidial Germination of Sapstain and Mold Fungi," Abstract, prepared for the May 10–15, 1992 meeting of the International Research Group on Wood Preservation, Harrowgate, U.K., believed to be distributed in Feb. or Mar. of 1992.

*Primary Examiner*—Douglas W. Robinson
*Assistant Examiner*—Maria Luisa Osoteo
*Attorney, Agent, or Firm*—M. Howard Silverstein; John D. Fado; Janet I. Stockhausen

[57] ABSTRACT

A method for retarding the growth of wood-degrading fungi by treating the wood with an effective amount of viable, nonsporulating *Streptomyces rimosus* SC-36 NRRL 21063.

1 Claim, 1 Drawing Sheet

BIOLOGICAL TREATMENT FOR CONTROLLING WOOD DETERIORATING FUNGI

FIELD OF THE INVENTION

This invention is a method for the treatment of wood and wood products with living actinomycete cells of *Streptomyces rimosus* non-sporulating isolate SC-36, NRRL 21063, for the purpose of preventing or retarding the reproduction and growth of wood deteriorating fungi. The metabolites of a *Streptomyces rimosus* non-sporulating isolate, designated herein as SC-36, has been found to be particularly effective in preventing basidiospore and conidia germination of wood-attacking fungi. The effect of combining diluted boron with such metabolites, as well as combining the metabolites with ethylene glycol, have been found to have a synergistic effect in preventing such germination.

BACKGROUND OF THE INVENTION

Actinomycetes, such as *Streptomyces rimosus*, are well known actinomycetes useful for the production of antibiotics (see U.S. Pat. Nos. 2,516,080 to Ben A. Sobin et al and 2,963,401 to Jacob W. Davison et al). A new strain of such *Streptomyces rimosus* is disclosed by U.S. Pat. No. 3,377,242 to Donald Lefemmine et al.

It has now been discovered that actinomycetes such as those described in the above references and extracts from such actinomycetes are particularly useful in treating and preventing fungal attack on wood as well as their antibiotic uses. Such use constitutes a significant advance in the treatment of wood for this purpose because there are environmental and health concerns about many of the synthetic chemical fungicides presently used to protect wood from fungal attack.

It is accordingly the object of the present invention to provide a means for retarding, stopping and preventing the fungal attack of wood by the treatment of such wood with living actinomycete cells.

It is also an object of the present invention to treat wood with the metabolites, i.e. a cell-free supernatant or a reconstituted cell-free compsotion, of the actinomycete to retard, stop or prevent fungal attack.

It is also an object of the present invention to treat wood with the actinomycete living cells of *Streptomyces rimosus* non-sporulating isolate SC-36 for the purpose of preventing, retarding or stopping fungal attack.

A further object of the present invention is to treat wood with a metabolite extract from the actinomycete *Streptomyces rimosus* non-sporulating isolate SC-36 for the purpose of preventing, retarding or stopping fungal attack.

A still further object of the present invention is to treat wood with a combination of a metabolic extract of the actinomycete *Streptomyces rimosus* non-sporulating isolate SC-36 and diluted boron for its synergistic effect in preventing, retarding or stopping fungal attack.

SUMMARY OF THE INVENTION

It has now been discovered that living actinomycete cells prevent, retard or stop basidiospore and conidia germination of wood-attacking fungi. There has been particular success with *Streptomyces rimosus* non-sporulating isolate we have designated as SC-36 (NRRL 21063). It has also been discovered that the metabolites of *Streptomyces rimosus* nonsporulating isolate SC-36 are particularly effective against wood-attacking fungi and particularly where such metabolites are combined with diluted boron. In the latter instance there is a synergistic antifungal effect.

These treatments completely prevented wood degradation and discoloration of sapstain fungi, mold fungi, brown-rot fungi and white-rot fungi in laboratory wood block tests and in pine log sections exposed in field trials. The combination of diluted ethylene glycol and these metabolites also inhibited basidiospore germination of brown-rot and white-rot fungi.

DETAILED DESCRIPTION OF THE INVENTION

Figure 1:
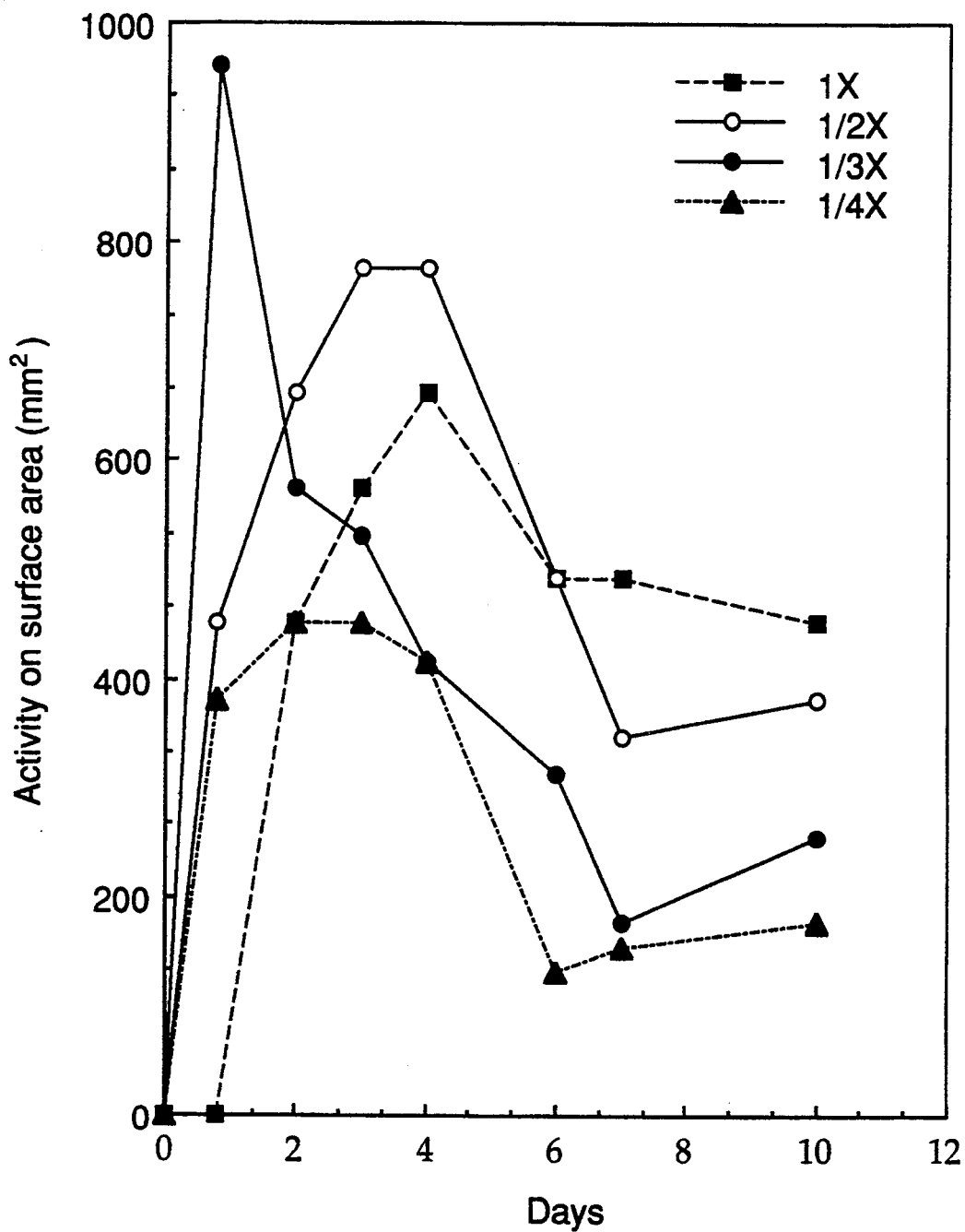
FIG. 1 is a graph of the effect of SB medium concentration on production of antifungal metabolites from *Streptomyces rimosus*, SC-36, in Aspergillus plate bioassay over time.

In the practice of the present invention a new strain of actinomycete isolate, *Streptomyces rimosus* non-sporulating isolate SC-36, specifically *S. rimosus* SC-36, NRRL 21063, under proper culture conditions, described below, produces potent antifungal metabolites and living actinomycete cells in complete liquid medium (CLM). *S. rimosus* was deposited at Agricultural Research Culture Collection (NRRL) International Depository Authority (Peoria, Ill.), at accession number 21063 on Apr. 1, 1992. The CLM medium may contain, per liter: D-glucose, 10 g; yeast extract, 5 g; lactalbumin hydrolysate, 15 g; sucrose, 2.8 g; calcium carbonate, 1 g. Mycelia from nutrient agar supplemented with 1% bacto peptone (NAP) slant are inoculated into 30 ml of CLM medium in 125-mml Erlenmeyer flasks and incubated at 30° C. with vigorous shaking on a platform shaker at 200 r/min for 1-2 days. The settled growth is transferred into 200-ml CLM medium in 500-ml Erlenmeyer flasks and allowed to grow for an additional 2-3 days. The harvested and packed actinomycete cells are suspended in equal volumes of 0.5% sodium chloride solution. Treatment of wood and wood-products with the actinomycete cells provided for application as a biological control agent of wood-attacking microorganisms.

For metabolite production, the cultural conditions recommended for the above consists of stock cultures of *Streptomyces rimosus* SC-36 maintained on nutrient agar supplemented with 1% peptone (NAP) slants. Cultures are grown in vegetative growth medium, 1x sporulation broth (SB), for activation and adaptation of inoculum. The sporulation broth medium contains per liter: 1.0 g yeast extract, 1.0 g beef extract, 2.0 g tryptose, 1 mg FeSO$_4$, and 10.0 g glucose. The pH of medium is adjusted to 7.2 before autoclaving. For vegetative growth, mycelia of SC-36 from cultures grown on a NAP slant for 5 days are scraped from the entire surface of the slant and cultured in 50 ml of SB medium in 125-ml Erlenmeyer flasks and incubated at 27° C. with vigorous shaking on a platform shaker at 200 r/min for 1-2 days. All cultures grow well in 1x SB medium, producing small (0.1-3 mm) pellets with average diameter of 0.2 to 0.4 mm. Approximately 3,000 to 5,000 small pellets are formed in 50 ml of growth medium in a 125-ml Erlenmeyer flask. The settled pellet is transferred into 100 ml of SB medium in 250-ml flasks and allowed to grow for an additional 40 h. The settled pellet-inoculum (100%) was then transferred into 50 ml of SB medium at various concentrations supplemented with 0.05%

Tween 20 in 125-ml Erlenmeyer flasks to find the production medium. Flasks are incubated at 30° C. at 200 r/min.

Antifungal activity is determined over time by measuring the clear-zone-diameter around the wells with 25 ul of metabolites in Aspergillus (*Aspergillus niger*) plate bioassay. Doubling the metabolite concentration increased the diameter of the clear-zone area around wells by 2 to 3 mm. The best results are obtained with the ½x concentration in the clear-zone area around the wells after 19 h. Therefore, ½x SB medium is used as the production medium (see FIG. 1 and Table 1). The volume of the culture and flask size do not influence the development of antifungal activity in the plate bioassay when they are varied proportionately. The activity is the same in 125-ml Erlenmeyer flasks with 50 ml medium and in 1,000-ml Erlenmeyer flasks with 400 ml of the same caused by synchrony in culture development. The pellets are recycled continuously for several months. The pellets can be recycled as long as they remain uncontaminated. The antifungal metabolites which are found in the culture fluid, can be harvested every day. Production, and thereby harvest frequency, can be controlled by the quantity and type of nutritional supplements provided to the pellets. Fermentation is enhanced, scaled up, and accelerated by promoting secondary metabolism and inhibiting biomass production using large (100%) and microscopic pellet-inoculum of the new strain, Streptomyces rimosus (SC-36) with a new production medium (½x), and by varying culture volume and shaking speed. The cessation of pellet growth signals secondary metabolism. Treatment of wood and wood products with metabolites or the synergistic effect of diluted or undiluted metabolites and diluted boron also provided for application as biological control agents of wood-atacking fungi. The combination of diluted metabolites and diluted glycol ethylene inhibits basidiospore germination of wood-rotting fungi and therefore, prevents wood deterioration, After following the above procedures inhibition of radial growth of sapstain and mold fungi was accomplished. The antagonistic effect of *Streptomyces rimosus* (SC-36) against various sapwood-inhabiting fungi was tested in petri plate assays. The growth of all the sapwood-inhabiting fungi tested was inhibited at a considerable distance, leaving a clear zone of inhibition between the fungi and *Streptomyces rimosus* (SC-36) on nutrient agar (NA) plates after 20 days of incubation. *Streptomyces rimosus* (SC-36) inhibited 81% to 86% of the radial growth of the fungi in the petri plates (Table 2).

The results of the interaction between wood-attacking fungi and metabolites in plate bioassay on 2% malt extract agar plates are given in Table 3. A basidiospore and conidia suspension of wood-attacking fungi (500,000 basidiospore for wood-rotting fungi or 200,000 conidia for sapstain and mold fungi) was spread into the surface of 2% malt extract agar plates. The basidiospore and conidia germination of all wood-attacking fungi was inhibited by 25 ul of 1-day-old metabolites from the production medium (½x) introduced in each well. The conidia and basidiospore germination of wood-attacking fungi was completely inhibited, leaving a clear-zone around the wells. The diameter of the inhibition or clear-zone are varied from 18 to 38 mm per 25 ul of crude metabolites or from 891 to 3,971 mm$^3$ per 25 ul of metabolites.

The antagonistic characteristics of the combination of diluted boron and diluted metabolites from *Streptomyces rimosus* SC-36 against various wood-attacking fungi tested in the petri plate bio-assay are shown in Table 4. A basidiospore or conidial suspension of wood-attacking fungi (500,000 basidiospore or 200,000 conidia) was spread onto the surface of 2% malt extract agar plates. Diluted (½x) or undiluted (1x) metabolites with or without a boron-containing co-biocide, namely disodium octaborate tetrahydrate ($Na_2B_8O_{13}4H_2O$), was added to the precut wells. The boron-containing co-biocide which provided the desired level of effectiveness is marketed by US Borax Inc. under the registered tradename TIM-BOR. The clear-zone-diameter around the wells was measured after incubation at 27° C. and 70% relative humidity for 2 to 10 days. The growth of all the wood-attacking fungi tested was not affected by either TIM-BOR (4% BAE) or diluted metabolites (½) alone. However, basidiospore or conidia germination of wood-attacking fungi was inhibited by combination treatments with diluted (½) metabolites from *Streptomyces rimosus* SC-36 and TIM-BOR (4% BAE) in the plate bioassay. In fact, the combination of diluted metabolites and TIM-BOR produced a synergistic effect that increased the antifungal activity by showing clear-zone area around the wells. The combination resulted in a synergistic effect that was more effective in the clear-zone area around the wells than that of undiluted metabolites (Table 4). The antifungal activity increased up to 23x by by *Ceratocystis pilifera* (Table 4). Doubling the metabolite concentration typically increased the diameter of the clear-zone area around the wells by 2 to 3 mm (S.D. 1.4, 1.6 respectively).

Table 5 shows that treatment of wood blocks with living actinomycete cells of *Streptomyces rimosus* (SC-36) completely inhibited basidiospore or conidia germination. After actinomycete cells were removed by washing with a stream of water at the end of incubation, the underlying wood was free of fungal attack, discoloration, or deterioration.

Table 6 shows the inhibition of basidiospore germination on blocks of Southern Yellow Pine (Pinus sp) inoculated with brown-rot fungi and blocks of sweetgum (*Liquidambar styraciflua* L.) inoculated with white-rot fungi. Blocks were treated with a combination of diluted boron and diluted metabolites of *Streptomyces rimosus* SC-36 for controlling wood-rotting fungi using the soil-block procedure (ASTM 1917) with one-half million basidiospore inoculum instead of mycelial plug. The undiluted metabolites (1x) and the combination of diluted boron (0.5% boric acid equivalent, BAE) and diluted metabolites (½x) of *Streptomyces rimosus* SC-36 on wood blocks completely inhibited basidiospore germination of the brown-rot fungi, *Gloeophyllum trabeum* and *Antrodia carbonica*, and the white-rot fungi, *Phanerocheate chrysosporium* and *Trametes versicolor*, and therefore prevented wood deterioration. Neither diluted metabolites nor diluted boron inhibited basidiospore germination of brown-rot and white-rot fungi after 12- to 16-week incubation. However, diluted metabolites prevented weight losses by 95 to 100% (Table 6).

Table 7 shows inhibition of basidiospore germination on wood blocks of Southern Yellow Pine (Pinus sp.) inoculated with brown-rot fungi and blocks of sweetgum (*Liquidambar styraciflua* L.) inoculated with white-rot fungi. Blocks were treated with a combination of diluted ethylene glycol and diluted metabolites of *Streptomyces rimosus* SC-36 for controlling wood-rotting fungi using the soil-block procedure (ASTM 1917) with one-half million basidiospore inoculum. Wood blocks treated with water for control or diluted ethylene glycol (40%) were unable to protect the wood from fungal growth. However, undiluted metabolites (1x) or the mixture of the diluted ethylene glycol (40%) and diluted metabolites (¼x) inhibited basidiospore germination of wood-rotting fungi and therefore prevented weight losses in wood blocks after 12- to 16-week incubation at 27° C. and 70% relative humidity (Table 7). The mixture of metabolites (¼x) and ethylene glycol demonstrated a synergistic effect.

Table 8 shows control of sapstain and mold fungi on wood blocks by the combination of diluted boron and undiluted metabolites of *Streptomyces rimosus* SC-36. Blocks of two wood species, Pinus sp. (Southern Pine) and *Liquidambar styraciflua* L. (sweetgum) were used. Blocks were presoaked to duplicate the moisture content of green wood and presterilized at normal atmospheric pressure and then were dipped for 60 seconds into each treatment: distilled water for control, TIM-BOR (1%, 2%, and 4% boric acid equivalent, BAE), metabolites (diluted, ¼x; undiluted 1x; concentrated, 10x), and the mixture of diluted TIM-BOR and diluted (¼x) or undiluted metabolites. These were then inoculated with 400,000 to 500,000 conidia of sapstain or mold fungi and were incubated at 27° C. and 70% relative humidity. The mixture of both combinations of TIM-BOR (4% BAE) and undiluted metabolites produced a synergistic effect that inhibited spore germination of sapstain and mold fungi on wood blocks as effectively as 10x metabolites and therefore prevented wood discoloration and deterioration.

Table 9 shows control of wood-attacking fungi on green pine log sections by living actinomycete cells, concentrated metabolites, and the combination of diluted boron and unconcentrated metabolites of *Streptomyces rimosus* SC-36. The green Southern Pine sapwood log sections were dipped for 60 seconds into each treatment. The results of the field or simulated field trials of living actinomycete cells or the combination of unconcentrated metabolites and diluted boron on pine log sections inhibited conidia and basidiospore germination of all wood-attacking fungi (Table 9). For the field trials, the treated log sections were hung on a fence for 8 weeks during the summer at the Vally View test site near Madison, Wis. The simulated field trials were undertaken using an air-permeable polypropylene bag containing soil from the test site. Microorganisms existing in the soil were restricted within the bag and the entire bag was incubated for 8 weeks at 27° C. and 70% humidity. Green Southern yellow pine sapwood log sections treated with either sodium pentachlorophenate (0.1%) or 4% boron (boric acid equivalent, BAE, of TIM-BOR) were unable to protect the wood from fungal growth. However, the combination of unconcentrated metabolites and 4% boron resulted in a synergistic effect that gave greater inhibition of basidiospore and conidia germination of all the wood-attacking fungi than that of concentrated metabolites or the TIM-BOR alone (Table 9). When the treated green Southern pine sapwood log sections were cut just below the area where the living actinomycete cells had been applied, these sections were free of fungal attack, discoloration, or deterioration. These treatments did not alter the physical state of the wood. Even after actinomycete cells (SC-36) had dried up, the pine log sections continued to be protected from wood-attacking fungi, and therefore the nondecayed living actinomycete cells are believed to be useful for long-term protection of wood against sapstain, mold, and wood-rotting fungi without altering the ecosystem.

Mostly purified abiotic metabolites are relatively nontoxic with an $LD_{50}$ of 1400 mg/kg when injected intraperitoneal into 20-g mouse.

0.09 mg abiotic metabolites inhibited conidia germination of *Aspergillus niger* by showing a 25–31 mm diameter clear-zone (2,156 mm$^3$) around the wells in the plate bioassay.

TABLE 1

Effect of SB medium concentration on production of antifungal metabolites from *Streptomyces rimosus* SC-36 in Aspergillus plate bioassay

| SM medium[b] concentration | Inhibition zone[a] | | Maximum Activity |
|---|---|---|---|
| | Diameter (mm/25 ul) | Area (mm$^2$/25 ul) | |
| 1x | 28.5 (0.7) | 638 (0.4) | 4 days |
| ½x | 31.0 (1.4) | 755 (1.5) | 3–4 days |
| ⅓x | 34.5 (2.1) | 940 (3.5) | 19 hours |
| ¼x | 23.5 (0.7) | 435 (0.4) | 2 days |

[a]Standard deviation in parentheses.
[b]SB is sporulation broth.

TABLE 2

Inhibition of radial growth of sapwood-inhabiting fungi by *Streptomyces rimosus* SC-36 in petri plate assay

| Fungus | Inhibition of radial growth[a] (percent) |
|---|---|
| Sapstain | |
| *Aureobasidium pullulans* | 86.0 (2.9) |
| *Ceratocystis coerulescens* | 84.6 (2.4) |
| *C. minor* | 84.6 (0.9) |
| *C. pilifera* | 81.3 (1.8) |
| Mold fungi | |
| *Aspergillus niger* | 84.5 (1.6) |
| *Penicillium* spp. | 85.6 (11.0) |
| *Trichoderma* spp. | 81.2 (1.6) |

[a]Standard deviation in parentheses.

TABLE 3

Inhibition of basidiospore and conidia germination of wood-attacking fungi by metabolites from *Streptomyces rimosus* SC-36 in plate bioassay on 2 percent malt extract agar[a]

| Fungus | Inhibition zone[b] | |
|---|---|---|
| | Diameter (mm/25 ul) | Volume (mm$^3$/25-ul) |
| Brown-rot fungi | | |
| *Gloeophyllum trabeum* | 22.0 (2.8) | 1,331 (22) |
| *Neolentinus lepideus* | 26.5 (2.1) | 1,946 (12) |
| Mold fungi | | |
| *Aspergillus niger* | 31.3 (1.2) | 2,694 (4) |
| *Penicillium* spp. | 19.3 (1.2) | 1,024 (4) |
| *Trichoderma* spp. | 28.0 (1.2) | 2,156 (4) |
| Sapstain | | |
| *Aureobasidium pullulans* | 30.0 (2.0) | 2,475 (11) |
| *Ceratocystis coerulescens* | 38.0 (2.0) | 3,971 (11) |
| *C. minor* | 32.7 (1.2) | 2,959 (4) |
| *C. pilifera* | 18.0 (1.2) | 891 (4) |
| White-rot fungi | | |
| *Phanerochaete chrysosporium* | 31.0 (1.4) | 2,643 (5) |
| *Schizophyllum commune* | 31.5 (2.1) | 2,746 (12) |
| *Trametes versicolor* | 31.0 (1.4) | 2,643 (5) |

[a]The clear-zone-diameter around the wells was measured after incubation at 27° C. and 70% relative humidity for two to ten days.
[b]Standard deviation in parentheses.

TABLE 4

Inhibition of conidia and basidiospore germination by metabolites of *Streptomyces rimosus* SC-36 with TIM-BOR as a co-biocide for controlling wood-attacking fungi in malt extract agar plate bioassay[a]

| Wood-attacking fungi | Inhibition zone | | | |
|---|---|---|---|---|
| | TIM-BOR 4% BAE | Metab 1X | Metab ¼X | ¼x Met TIM-BOR |
| Brown rot fungi | | | | |
| *Gleophyllum trabeum* | 0 | 20–22 | 0 | 35–36 |
| Mold fungi | | | | |
| *Aspergillus niger* | 0 | 25–27 | 0 | 30–32 |
| *Penicillium* spp. | 0 | 20–22 | 0 | 26–32 |
| *Trichoderma* spp. | 0 | 25–28 | 0 | 35–37 |
| Sapstain fungi | | | | |
| *Aureobasidium pullulans* | 0 | 30–33 | 0 | 18–20 |
| *Ceratocystis coerulescens* | 0 | 36–39 | 0 | 36–38 |
| *C. minor* | 0 | 24–26 | 0 | 33–35 |
| *C. pilifera* | 0 | 10–18 | 0 | 28–30 |
| White rot fungi | | | | |
| *Phanerochaete chrysosporium* | 0 | 30–32 | 0 | 30–36 |
| *Schizophyllum commune* | 0 | 30–33 | 0–10 | 33–35 |
| *Trametes versicolor* | 0 | 30–32 | 0 | 30–31 |

[a]The clear-zone-diameter around the wells was measured after incubation at 27° C. and 70% relative humidity for two to ten days.

TABLE 5

Inhibition of conidia and basidiospore germination on wood blocks treated with living actinomycete cells of *Streptomyces rimosus* SC-36 for controlling wood-rotting fungi.

| | Basidiospore and conidia germination[a] | | | |
|---|---|---|---|---|
| | Control | | Living actinomycete cells | |
| Wood-attacking fungi | Gum | Pine | Gum | Pine |
| Brown-rot fungi | | | | |
| *Antrodia carbonica* | 4 | 4 | 0 | 0 |
| *Gloeophyllum trabeum* | 4 | 4 | 0 | 0 |
| *Neolentinus lepideus* | 4 | 4 | 0 | 0 |
| *Postia placenta* | 4 | 4 | 0 | 0 |
| Mold fungi | | | | |
| *Aspergillus niger* | 4 | 4 | 0 | 0 |
| *Penicillium* spp. | 4 | 4 | 0 | 0 |
| *Trichoderma* spp. | 4 | 4 | 0 | 0 |
| Stain fungi | | | | |
| *Aureobasidium pullulans* | 4 | 4 | 0 | 0 |
| *Ceratocystis coerulescens* | 4 | 4 | 0 | 0 |
| *C. minor* | 4 | 4 | 0 | 0 |
| *C. pilifera* | 4 | 4 | 0 | 0 |
| White-rot fungi | | | | |
| *Phanerochaete chrysosporium* | 4 | 4 | 0 | 0 |
| *Schizophyllum commune* | 4 | 4 | 0 | 0 |
| *Trametes versicolor* | 4 | 4 | 0 | 0 |

[a]The blocks were rated for fungal growth or stain after 8 to 10 weeks exposure at 27° C. and 70% relation humidity using the following scale:
0 Clean: no stain or mold
1 Minor: stain or mold covering less than 5% of upper surface.
2 Light stain: stain or mold covering 5–20% of upper surface.
3 Moderate stain: stain or mold covering 20–40% of upper surface.
4 Heavy stain: stain or mold covering more than 40% of upper surface.

TABLE 6

Inhibition of basidiospore germination on wood blocks of Southern Yellow Pine for brown-rot fungi and wood blocks of sweetgum (*Liquidambar styraciflue* L.) for white-rot fungi treated with the combination of diluted boron (Tim-Bor) and/or diluted metabolites of *Streptomyces rimosus* (SC-36) for controlling wood-rotting fungi using soil-block procedure (ASTM 1917).

| | Basidiospore germination[a] and weight loss[b] | | | | | | | |
|---|---|---|---|---|---|---|---|---|
| | Brown-rot Fungi | | | | White-rot Fungi | | | |
| | *Antrodia carbonica* | | *Gloeophyllum trabeum* | | *Phanerochaete chrysosporium* | | *Trametes versicolor* | |
| Treatment | Growth | % wt loss | Growth | % wt loss | Growth | % wt loss | Growth | % wt loss |
| Control | 4 | 1.3 (0.1) | 4 | 37.5 (2.8) | 4 | 25.9 (8.2) | 4 | 27.7 (8.9) |
| 0.25% BAE | 3 | 1.9 (0.8) | 4 | 29.4 (4.7) | 4 | 6.3 (3.6) | 4 | 16.0 (7.2) |
| 0.5% BAE | 2–3 | 0.6 (0.8) | 4 | 24.3 (4.3) | 4 | 4.0 (1.5) | 4 | 0 |
| 1.0% BAE | 0 | 0 | 4 | 22.1 (4.4) | 4 | 5.7 92.0) | 2 | 0 |
| 2% BAE | 0 | 0 | 2 | 0.2 (0.5) | 2 | 2.9 (2.1) | 2 | 0 |
| Metabolites (¼x) | 3 | 0 | 3 | 0 | 4 | 1.3 (1.3) | 2 | 0 |
| ¼X metabolites + 0.5% BAE | 0 | 0 | 0 | 0 | 0 | 0 | 0 | 0 |
| Undiluted metabolites | 0 | 0 | 0 | 0 | 0 | 0 | 0 | 0 |

[a]The blocks were rated for the fungal growth after 12–16 weeks exposure at 27° C. using the following scale:
0, no growth; 1, slight growth; 2, poor growth; 3, moderate growth; 4, good growth based on the control.
[b]Standard deviation in parenthesis (%).

TABLE 7

Inhibition of basidiospore germination on wood blocks of Southern Yellow Pine for brown-rot fungi and wood blocks of sweetgum (*Liquidambar styraciflua* L.) for white-rot fungi treated with the combination of diluted ethylene glycol and metabolites of *Streptomyces rimosus* (SC-36) for controlling wood-rotting fungi using soil-block procedure (ASTM 1917).

| | Basidiospore germination[a] and weight loss[b] | | | | | | | |
|---|---|---|---|---|---|---|---|---|
| | Brown-rot Fungi | | | | White-rot Fungi | | | |
| | *Antrodia carbonica* | | *Gloeophyllum trabeum* | | *Phanerochaete chrysosporium* | | *Trametes versicolor* | |
| Treatment | Growth | % wt loss | Growth | % wt loss | Growth | % wt loss | Growth | % wt loss |
| Control | 4 | 1.3 (0.1) | 4 | 37.5 (2.8) | 4 | 25.9 (8.2) | 4 | 27.7 (8.9) |
| Ethylene glycol (40%) | 4 | 1.9 (0.9) | 4 | 21.7 (4.3) | 4 | 28.4 (6.9) | 4 | 39.3 (17.7) |
| Metabolites (¼x) | 3 | 0 | 3 | 0 | 4 | 1.3 (1.3) | 2 | 0 |
| Metabolites (¼x + ethylene glycol) | 0 | 0 | 0 | 0 | 0 | 0 | 0 | 0 |

TABLE 7-continued

Inhibition of basidiospore germination on wood blocks of Southern Yellow Pine for brown-rot fungi and wood blocks of sweetgum (*Liquidambar styraciflua* L.) for white-rot fungi treated with the combination of diluted ethylene glycol and metabolites of *Streptomyces rimosus* (SC-36) for controlling wood-rotting fungi using soil-block procedure (ASTM 1917).

| | Basidiospore germination[a] and weight loss[b] | | | | | | | |
|---|---|---|---|---|---|---|---|---|
| | Brown-rot Fungi | | | | White-rot Fungi | | | |
| | Antrodia carbonica | | Gloeophyllum trabeum | | Phanerochaete chrysosporium | | Trametes versicolor | |
| Treatment | Growth | % wt loss | Growth | % wt loss | Growth | % wt loss | Growth | % wt loss |
| Undiluted metabolites | 0 | 0 | 0 | 0 | 0 | 0 | 0 | 0 |

[a] The blocks were rated for the fungal growth after 12–16 weeks exposure at 27° C. using the following scale:
0, no growth; 1, slight growth; 2, poor growth; 3, moderate growth; 4, good growth based on the control.
[b] Standard deviation in parenthesis (%).

TABLE 8

Inhibition of conidia germination on wood blocks by metabolites from *Streptomyces rimosus* SC-36 with boron co-biocide for controlling mold fungi and sapstain.

| | Degree of discoloration[a] | | | | | | | | | | | | | |
|---|---|---|---|---|---|---|---|---|---|---|---|---|---|---|
| | Mold fungi | | | | | | Saptain | | | | | | | |
| | Aspirgillus niger | | Penicillium sp. | | Trichoderma sp. | | Aureobasidium pullulans | | Ceratocystis coerulescens | | Ceratocyctis minor | | Ceratocystis pilifera | |
| Treatment | Gum | Pine | Gum | Pine | Gum | Pine | Gum | Pine | Gum | Pine | Gum | Pine | Gum | Pine |
| Control | 4 | 4 | 4 | 4 | 4 | 4 | 4 | 4 | 4 | 4 | 4 | 4 | 4 | 4 |
| 1% BAE | 4 | 4 | 4 | 4 | 4 | 4 | 4 | 4 | 4 | 4 | 4 | 4 | 4 | 4 |
| 2% BAE | 4 | 4 | 4 | 4 | 4 | 4 | 4 | 4 | 4 | 4 | 4 | 2 | 4 | 4 |
| 4% BAE | 3 | 3 | 4 | 4 | 4 | 4 | 4 | 4 | 4 | 4 | 4 | 2 | 4 | 4 |
| Metabolites (¼x) | 4 | 4 | 4 | 4 | 4 | 4 | 4 | 4 | 4 | 4 | 4 | 4 | 4 | 4 |
| Metabolites (¼x) | | | | | | | | | | | | | | |
| + 1% BAE | 4 | 4 | 4 | 4 | 4 | 4 | 4 | 4 | 4 | 4 | 4 | 4 | 4 | 4 |
| + 2% BAE | 4 | 4 | 2 | 2 | 4 | 4 | 4 | 4 | 4 | 4 | 1 | 1 | 3 | 1 |
| + 4% BAE | 2 | 2 | 0 | 0 | 0 | 1 | 4 | 4 | 0 | 0 | 0 | 0 | 1 | 0 |
| Metabolites (1x) | 4 | 4 | 3 | 3 | 4 | 4 | 1 | 3 | 3 | 1 | 1 | 0 | 1 | 0 |
| Metabolites (1x) | | | | | | | | | | | | | | |
| + 2% BAE | 3 | 3 | 1 | 1 | 3 | 1 | 0 | 0 | 0 | 1 | 0 | 0 | 0 | 0 |
| + 4% BAE | 0 | 0 | 0 | 0 | 0 | 0 | 0 | 0 | 0 | 0 | 0 | 0 | 0 | 0 |
| Metabolites (10x) | 0 | 0 | 0 | 0 | 0 | 0 | 0 | 0 | 0 | 0 | 0 | 0 | 0 | 0 |

[a] The blocks were rated for the fungal growth or stain after 8 weeks exposure at 27° C. using the following scale:
0 Clean: no stain or mold.
1 Minor: stain or mold covering less than 5% of upper surface.
2 Light stain: stain or mold covering 5–20% of upper surface.
3 Moderate stain: stain or mold covering 20–40% of upper surface.
4 Heavy stain: stain or mold covering more than 40% of upper surface.

TABLE 9

Inhibition of wood-attacking fungi or pine log sections treated with living actinomycete cells, metabolites (1x or 10x), and metabolites from *Streptomyces rimosus*, SC-36, with diluted boron as a co-biocide (Exposed in a simulated field test or in field trails*)

| Treatment | Rating for fungal growth[a] or stain |
|---|---|
| Control | 4 |
| 0.1% PCP | 4 |
| 4% BAE boron | 4 |
| metabolites (1x) | 1* or 2 |
| metabolites (1x) + boron (4% BAE) | 0* or 0–1 |
| metabolites (1ox) | 1* or 1–2 |
| Living actinomycete cells | 0 |

[a] The pine log sections were rated for the fungal growth or stain of wood-attacking fungi after 8 weeks simulated field exposure at 27° C. and 70% relative humidity or field trails* using the following scale:
0 Clean: no stain or mold
1 Minor: stain or mold covering less than 5% of upper surface.
2 Light stain: stain or mold covering 5–20% of upper surface.
3 Moderate stain: stain or mold covering 20–40% of upper surface.
4 Heavy stain: stain or mold covering more than 40% of upper surface.

Having thus described the invention in its preferred embodiment, it will be clear that modifications may be made without departing from the spirit of the invention. Also the language used to describe the inventive concept and the drawings accompanying the application to illustrate the same are not intended to be limiting on the invention. Rather it is intended that the invention be limited only by the scope of the appended claims.

We claim:

1. A method for retarding growth of wood-degrading fungi on wood comprising treating said wood with an effective amount of viable, nonsporulating *Streptomyces rimosus* SC-36 NRRL 21063.

* * * * *